(12) United States Patent
Douglas et al.

(10) Patent No.: US 9,110,912 B2
(45) Date of Patent: Aug. 18, 2015

(54) STORAGE SYSTEMS AND METHODS

(75) Inventors: Eric Douglas, Los Gatos, CA (US); Christine Hao, Palo Alto, CA (US); Zachary Steinkamp, San Jose, CA (US)

(73) Assignee: Symantec Corporation, Mountain View, CA (US)

( * ) Notice: Subject to any disclaimer, the term of this patent is extended or adjusted under 35 U.S.C. 154(b) by 237 days.

(21) Appl. No.: 12/885,438

(22) Filed: Sep. 18, 2010

(65) Prior Publication Data

US 2011/0225266 A1 Sep. 15, 2011

Related U.S. Application Data

(60) Provisional application No. 61/267,362, filed on Dec. 7, 2009, provisional application No. 61/330,262, filed on Apr. 30, 2010.

(51) Int. Cl.
*G06F 17/30* (2006.01)
*G06F 19/00* (2011.01)

(52) U.S. Cl.
CPC ........ *G06F 17/30147* (2013.01); *G06F 19/321* (2013.01); *G06F 19/322* (2013.01)

(58) Field of Classification Search
None
See application file for complete search history.

(56) References Cited

U.S. PATENT DOCUMENTS

| | | | | |
|---|---|---|---|---|
| 6,430,611 B1 * | 8/2002 | Kita et al. | | 709/223 |
| 6,473,401 B1 * | 10/2002 | Kong et al. | | 370/229 |
| 2002/0099797 A1 * | 7/2002 | Merrell et al. | | 709/219 |
| 2004/0015724 A1 * | 1/2004 | Pham et al. | | 713/201 |
| 2006/0095664 A1 | 5/2006 | Wichelman et al. | | |
| 2006/0293868 A1 | 12/2006 | McCall et al. | | |
| 2007/0027929 A1 | 2/2007 | Whelan | | |
| 2007/0156842 A1 | 7/2007 | Vermeulen et al. | | |
| 2008/0177970 A1 * | 7/2008 | Prahlad et al. | | 711/170 |
| 2009/0037479 A1 * | 2/2009 | Bolik et al. | | 707/200 |
| 2009/0094320 A1 * | 4/2009 | Palthepu et al. | | 709/203 |
| 2010/0037049 A1 * | 2/2010 | Otis et al. | | 713/165 |

OTHER PUBLICATIONS

International Search Report and Written Opinion. PCT/US2010/059333; Date of Mailing Mar. 21, 2011.

* cited by examiner

*Primary Examiner* — Wei Zhao
*Assistant Examiner* — Ronald H Davis
(74) *Attorney, Agent, or Firm* — Wilmer Cutler Pickering Hale and Dorr LLP

(57) ABSTRACT

Systems and methods for extent reference count updates are presented. In one embodiment; a reference count update method includes: receiving a plurality of data files associated with various modalities; performing an analysis on the data files including examining an impact of the plurality of data files on storage based upon a type of the modality; and forwarding resulting analysis information for presentation in a convenient user interface, including an indication of the impact of the plurality of data files on the storage based upon the type of the modality. In one embodiment the analysis includes resource consumption analysis of the storage associated with the type of modality. The analysis can include a cost analysis of the storage associated with the type of modality. The storage can be included in a cloud environment.

13 Claims, 15 Drawing Sheets

200

```
┌─────────────────────────────────────────────┐
│   RECEIVING A PLURALITY OF DATA FILES       │
│                   210                       │
└─────────────────────────────────────────────┘
                      │
┌─────────────────────────────────────────────┐
│ PERFORMING ANALYSIS ON THE DATA FILES        │
│ INCLUDING EXAMINING AN IMPACT OF THE         │
│ PLURALITY OF DATA FILES ON STORAGE           │
│                   220                        │
└─────────────────────────────────────────────┘
                      │
┌─────────────────────────────────────────────┐
│ FORWARDING RESULTING ANALYSIS INFORMATION    │
│ FOR PRESENTATION IN A CONVENIENT USER        │
│ INTERFACE                                    │
│                   230                        │
└─────────────────────────────────────────────┘
```

```
┌─────────────────────────────────────────────────┐
│   RETRIEVING FILE CHARACTERISTIC INFORMATION    │
│                      310                        │
└─────────────────────────────────────────────────┘
                        │
┌─────────────────────────────────────────────────┐
│  PERFORMING AN ASSESSMENT OF THE IMPACT OF THE  │
│          FILE ON THE STORAGE SYSTEMS            │
│                      320                        │
└─────────────────────────────────────────────────┘
```

```
┌─────────────────────────────────────────────┐
│ RECEIVING A PLURALITY OF DATA FILES ASSOCIATED │
│         WITH VARIOUS MODALITIES              │
│                   510                        │
└─────────────────────────────────────────────┘
                      │
┌─────────────────────────────────────────────┐
│   PERFORMING AN ANALYSIS ON THE DATA FILES   │
│ INCLUDING EXAMINING AN IMPACT OF THE PLURALITY OF │
│  DATA FILES ON STORAGE BASED UPON A TYPE OF THE │
│                  MODALITY                    │
│                   520                        │
└─────────────────────────────────────────────┘
                      │
┌─────────────────────────────────────────────┐
│   FORWARDING RESULTING ANALYSIS INFORMATION FOR │
│    PRESENTATION IN A CONVENIENT USER INTERFACE, │
│ INCLUDING AN INDICATION THE IMPACT OF THE PLURALITY │
│  OF DATA FILES ON THE STORAGE BASED UPON THE TYPE │
│                 OF MODALITY                  │
│                   530                        │
└─────────────────────────────────────────────┘
```

FIGURE 5

| Symantec Health For Providers | Summary | Service | Studies | Appliances | Alerts | Users | | |
|---|---|---|---|---|---|---|---|---|
| Appliance Summary | | | | | | lisa_rom@symantec.com\|Logout\|Help | | |

| Query Controls | Appliances | Site | Studies/Day | Study Backlog | Days to Full | Alerts |
|---|---|---|---|---|---|---|
| Sites<br>>All Sites<br>South Central<br>South Central North<br>South Central West<br><br>Status<br>>All<br>Ok<br>Warning<br>Critical | Appliance_E | South Central Cardiology | 451 | ～～ 65 | ～～ 95 | None |
| | Appliance_F | South Central Cardiology | 148 | ～～ 46 | ～～ 103 | None |
| | Appliance_A | South Central North | 451 | ～～ 52 | ～～ 74 | Appliance failed to check in when required |
| | Appliance_B | South Central North | 148 | ～～ 36 | ～～ 97 | Power adapter failure |
| | Appliance_C | South Central West | 451 | ～～ 39 | ～～ 69 | Low Bandwidth |
| | Appliance_D | South Central West | 148 | ～～ 58 | ～～ 71 | None |

FIGURE 11

STORAGE SYSTEMS AND METHODS

RELATED APPLICATIONS

This application claims the benefit of and priority to Provisional Patent Application No. 61/267,362, entitled ELECTRONIC HEALTHCARE INITIATIVE filed on Dec. 7, 2009 and Provisional Patent Application No. 61/330,262 entitled ELECTRONIC HEALTH filed on date Apr. 30, 2010, which are both incorporated herein by this reference.

FIELD OF THE INVENTION

The present embodiments relate to the field of information storage.

BACKGROUND OF THE INVENTION

Electronic systems and circuits are often utilized in a number of applications to achieve advantageous results. Numerous electronic technologies such as computers, video equipment, and communication systems facilitate increased productivity and cost reduction in analyzing and communicating information in most areas of business, science, education and entertainment. Frequently, these activities involve storage of vast amounts of important and confidential information and significant resources are expended storing and processing the information. Maintaining and managing storage of the information often involves significant resources and skill sets. Accurately accessing the impacts (e.g., utilization, costs, etc.) of data storage on storage resources is often important.

SUMMARY

Systems and methods for storage are presented. In one embodiment; a storage method includes: receiving a plurality of data files associated with various modalities; performing an analysis on the data files including examining an impact of the plurality of data files on storage based upon a type of the modality; and forwarding resulting analysis information for presentation in a convenient user interface, including an indication of the impact of the plurality of data files on the storage based upon the type of the modality. In one embodiment the analysis includes resource consumption analysis of the storage associated with the type of modality. The analysis can include a cost analysis of the storage associated with the type of modality. The storage can be included in a cloud environment. The data files can be received in a cloud environment from a gateway at a remote location. In one embodiment, the data files are forwarded to the cloud environment from the gateway at the remote location in accordance with predetermined metrics. The data files can be forwarded back to the gateway when requested.

In one embodiment, a computer readable storage medium having stored thereon, computer executable instructions that, when executed by a computer system cause the computer system to perform a method. In one embodiment, the method includes: receiving a plurality of data files associated with various modalities; performing an analysis on the data files including examining an impact of the plurality of data files on storage based upon a type of the modality; and forwarding resulting analysis information for presentation in a convenient user interface, including an indication of the impact of the plurality of data files on the storage based upon the type of the modality. In one embodiment the analysis includes resource consumption analysis of the storage associated with the type of modality. The analysis can include a cost analysis of the storage associated with the type of modality. The storage can be included in a cloud environment. The data files can be received in a cloud environment from a gateway at a remote location. In one embodiment, the data files are forwarded to the cloud environment from the gateway at the remote location in accordance with predetermined metrics. The data files can be forwarded back to the gateway when requested.

In one exemplary implementation, a computer system has a processor coupled to a computer readable storage media and the computer system executes computer readable code which causes the computer system to perform operations including: receiving a plurality of data files associated with various modalities; performing an analysis on the data files including examining an impact of the plurality of data files on storage based upon a type of the modality; and forwarding resulting analysis information for presentation in a convenient user interface, including an indication of the impact of the plurality of data files on the storage based upon the type of the modality. In one embodiment the analysis includes resource consumption analysis of the storage associated with the type of modality. The analysis can include a cost analysis of the storage associated with the type of modality. The storage can be included in a cloud environment. The data files can be received in a cloud environment from a gateway at a remote location. In one embodiment, the data files are forwarded to the cloud environment from the gateway at the remote location in accordance with predetermined metrics. The data files can be forwarded back to the gateway when requested.

DESCRIPTION OF THE DRAWINGS

The accompanying drawings, which are incorporated in and form a part of this specification, are included for exemplary illustration of the principles of the present embodiments and not intended to limit the present invention to the particular implementations illustrated therein. The drawings are not to scale unless otherwise specifically indicated.

FIG. 2 is a flow chart of an exemplary information storage method in accordance with one embodiment of the present invention.

FIG. 3 is a block diagram of an exemplary data storage impact analysis process in accordance with one embodiment of the present invention.

FIG. 5 is flow chart of an exemplary information storage method in accordance with one embodiment of the present invention.

FIG. 11 is a block diagram of an exemplary appliance metrics by site and status selection presentation in accordance with one embodiment of the present invention.

DETAILED DESCRIPTION

Reference will now be made in detail to the preferred embodiments, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope as defined by the appended claims. Furthermore, in the following detailed description, numerous specific details are set forth in order to provide a thorough understanding. However, it will be obvious to one ordinarily skilled in the art that the present invention may be practiced without these specific details. In other instances, well known methods, procedures, components, and circuits have not been described in detail as not to unnecessarily obscure aspects of the current invention.

The present systems and methods facilitate efficient and effective information storage management. Present system and method archiving solutions can compliment existing infrastructures. Present systems and methods facilitate convenient tracking and management of data storage impact on storage resources. For example, present systems and methods can facilitate robust analysis on consumption of storage resources and the cost of the storage. The analysis can include diverse examination based upon a variety of parameters and metrics. The systems and methods can be utilized to analyze a plurality of different types of data files (e.g., image data files associated with different medical modalities, etc).

The analysis results can include costs of resources occupied by the different data files according to data file type. The analysis results can facilitate cost assignment and cost analysis associated with storage of the data. The secure alternative to onsite storage can provide pay per usage capacity on demand to facilitate reduction of costs and capital spending. Multiple images or copies can be archived in a plurality of resources (e.g., geographically distributed, high availability, etc.) utilized for data recovery.

Figure 1:
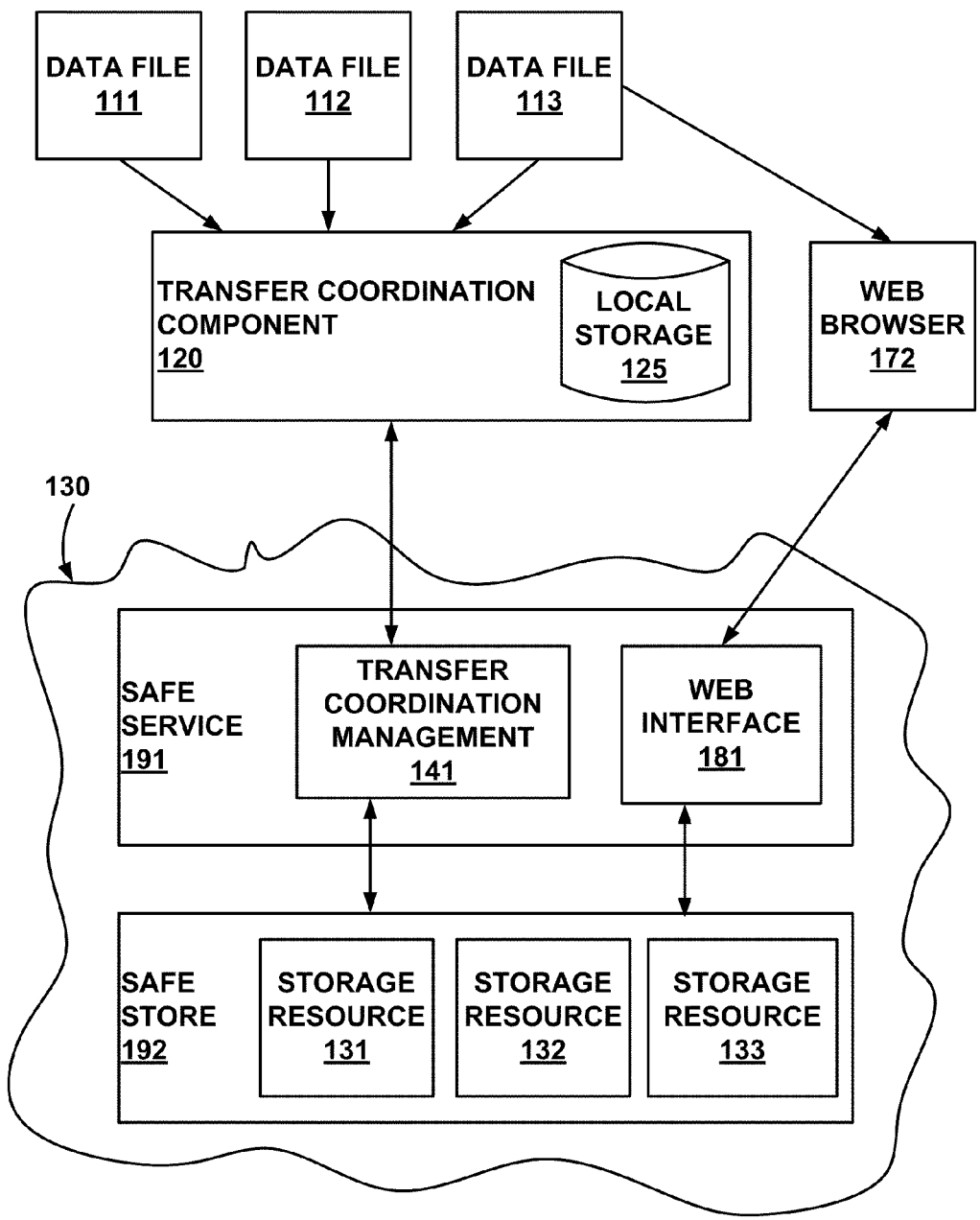
FIG. 1 is a block diagram of an exemplary file system storage architecture in accordance with one embodiment.

FIG. 1 is a block diagram of exemplary data storage system 100 in accordance with one embodiment of the present invention. Data storage system 100 includes data files 111, 112, and 113, transfer coordination component 120, cloud system 130, and web browser 172. Cloud system 130 includes safe service component 191 and safe store component 192. Safe service component 191 includes transfer coordination management component 141 and WEB interface 151. Safe store component 192 includes storage resource 131, 132 and 133. In one embodiment, data files 111, 112, and 113 are communicatively coupled to WEB browser 172 and transfer coordination component 120 which includes local storage 125. The components within cloud system 130 can be communicatively coupled to one another and to components outside the cloud (e.g., through transfer coordination component 120, transfer coordination management component 141, WEB interface 151, WEB browser 172, etc.).

The components of data storage system 100 cooperatively operate to facilitate efficient and effective storage of a plurality of data files. Data files 111, 112 and 113 are communicated to transfer coordination component 120. It is appreciated the data files can be associated with different types of data (e.g., different modalities, etc.). In one embodiment, the data files can be "pushed" or "pulled" into transfer coordination component 120. Transfer coordination component 120 coordinates transfer of the data file information to and from local storage 125 and cloud 130. The transfer coordination component 120 can be implemented in a variety of configurations (e.g., a gateway appliance, an upload component, a download component, combination upload and download component, etc.). It is also appreciated that data file information can be communicated to the cloud 130 via web interface 181. Within cloud 130, safe store component 192 stores the data file information. In one exemplary implementation, safe store component 191 utilizes storage resource 131, 132 and 133 to store the data file information in accordance with control by transfer coordination management component 141. In one embodiment, data files can also be uploaded via a web interface 181.

FIG. 2 is a flow chart of exemplary information storage method 200 in accordance with one embodiment of the present invention.

In block 210, a plurality of data files are received. In one embodiment the plurality of data files are received at centralized resources from remote locations. The centralized resources can be part of a cloud environment. In one exemplary implementation, the data files are associated with different types of data (e.g., different modalities, etc.). In one exemplary implementation, the data files are coordinated for transfer to a cloud environment. The coordination can include retrieving the data files from generation components (e.g. different modality generation components, etc.).

In block 220, analysis is performed on the data files including examining an impact of the plurality of data files on storage. In one embodiment, a data storage impact analysis process is performed on the data files. The data storage impact analysis can examine the amount of storage resources occupied by particular types of data files and the impact of that storage (e.g., cost, performance, etc.).

In block 230, resulting analysis information is forwarded for presentation in a convenient user interface. In one embodiment, various parameters or metrics associated with the plurality of files are presented and can include parameters or metrics associated with storage of the files. For example, the amount of storage resources occupied or consumed by the plurality of files, the cost of the storage, etc.

In one embodiment, resulting analysis information is forwarded for utilization in various management activities. The management activities can include preparing billing for various users, wherein the billing is based at least in part upon results from analysis in block 220. In one exemplary implementation, the billing can be based upon costs indicated by the analysis results of block 220, including indication of bandwidth and storage utilization. The billing can be prepared in a variety of different configurations, including breaking out or distinguishing bandwidth and storage consumption billing by time (e.g., per day, per month, etc) or type (e.g., high speed, compressed versus non-compressed data, high resolution versus low resolution, etc.). In one embodiment, the management activities include managing storage and communication resources. The analysis results from block 220 can be utilized in assignment, configuration, and utilization of storage resources. In one exemplary implementation, bandwidth and storage resources are assigned to users based in part upon the results of the analysis in block 220.

FIG. 3 is a block diagram of an exemplary data storage impact analysis method or process 300 in accordance with one embodiment of the present invention. Similar to block 220, the data storage impact process 300 can include examination of the amount of storage resources occupied by particular types of data files and the impact of that storage (e.g., cost, performance, etc.).

In block 310, file characteristic information is retrieved. In one embodiment, the file characteristic information can be observed as the file is received. For example, the file name can be extracted, file size can be measured, etc. In one embodiment, metadata associated with the file is examined. For example, metadata indicating the type of data file, the size of the file, date created, etc. can be examined. In one embodiment, the file can be compressed and the size of the file can be examined after compression.

In block 320, an assessment of the impact of the file on the storage systems is performed. In one embodiment, the assessment includes correlating the file characteristic information to system storage characteristics. For example, type of storage resource utilized to store the information, amount of time for the file to processed, the cost of storage for the file, the costs associated with processing the information, etc.

In one embodiment, analysis of bandwidth consumption and storage usage can include analysis of accesses to information. In one embodiment, the present systems and methods include a web application service enabling the secure sharing and collaboration of medical images. In one exemplary implementation the images can be accessed through a web site. Medical images can be uploaded in one embodiment through the web site in DICOM DIR format, or through a gateway appliance deployed within a remote location (e.g., medical facility, hospital) which has access to a PACS. Users are able to view images and share access to images with other users. Images can also be shared with users not registered with the web site. For example, via a two-factor email invitation and FAX PIN sign-up process. Once images are shared, users sharing the image may collaborate by exchanging notes within the context of the medical imaging study. Activities affecting image content, notes, and sharing invitations can be presented to users as an integral part of the application.

In one embodiment, an application service includes an image share service that accepts images (e.g., in DICOM format, etc.). Incoming images can be cataloged by examining attributes (e.g., DICOM attributes, etc.) and the images can then be encrypted and stored in a safe store internal storage system.

Images can be uploaded directly on the web site, or by a gateway appliance. Direct web site upload can be achieved through an uploader. In one embodiment, an application is able to media index files (e.g., DICOMDIR, etc.) and obtain a list of files that make up a medical imaging study. In one exemplary implementation the uploader uploads all DICOM files described in a DICOM DIR file to the service. The uploader can enable images to be uploaded immediately without the need for a Gateway.

In one embodiment, a gateway can enable a PACS to transmit images to the gateway via the DICOM protocol. In one exemplary implementation, the images are then uploaded to the safe service and safe store using HTTP over SSL. Gateway uploads can enable a large number of images to be uploaded everyday with no manual intervention.

In one embodiment, images can be logically organized into a "study" which represents the exam here a discrete set of images are captured by a medical imaging device. A users can have access to studies they've uploaded directly to the web site or studies that have been uploaded by a Gateway within their facility (e.g., hospital, medical office, etc.). In one exemplary implementation, a study is shared by navigating to the study's detail page within the service, then typing the name of a registered user or email address of a non-registered user. An email notification can be forwarded to a user indicating that a new study has been shared with him/her.

In one embodiment, when sharing with a non-registered user, the intended person's email address and FAX number are entered. The person will receive a URL within an email invitation that refers to a page on the web site that requires the PIN received via FAX to be entered. When the right combination of PIN is entered for an invitation URL, a person completes a brief sign-up process to become a registered user. Upon registration, the user is redirected to the shared study.

Two users collaborating on a study may exchange notes between each other. Notes can be private between two users, including when the study is shared among more than two given users. Notes between two users can be organized by and presented within the context of a specific study.

The ability to quickly find studies or other users is provided through a powerful search engine. Study meta data is indexed, along with user attributes. Users may refine search results by clicking additional search dimensions and/or typing additional filters in the search text.

In one embodiment, medical images can be manipulated by panning, zooming, rotating, flipping, and/or adjusting window level and center (similar to brightness/contrast). Some medical images are motion video, where the same manipulations must be made while videos are playing.

In one exemplary implementation, the web site includes an image viewer providing the manipulations mentioned above. The image viewer enables the manipulations to be made using the power of the end-user's computer hardware while preserving the efficiency of ease of access of a web application.

In one embodiment, actions involving a study (e.g., viewing, sharing, adding a note, downloading, etc.) are stored and presented to other users involved in the action. Auditing can be made an integral part of the application's functionality.

Figure 4:
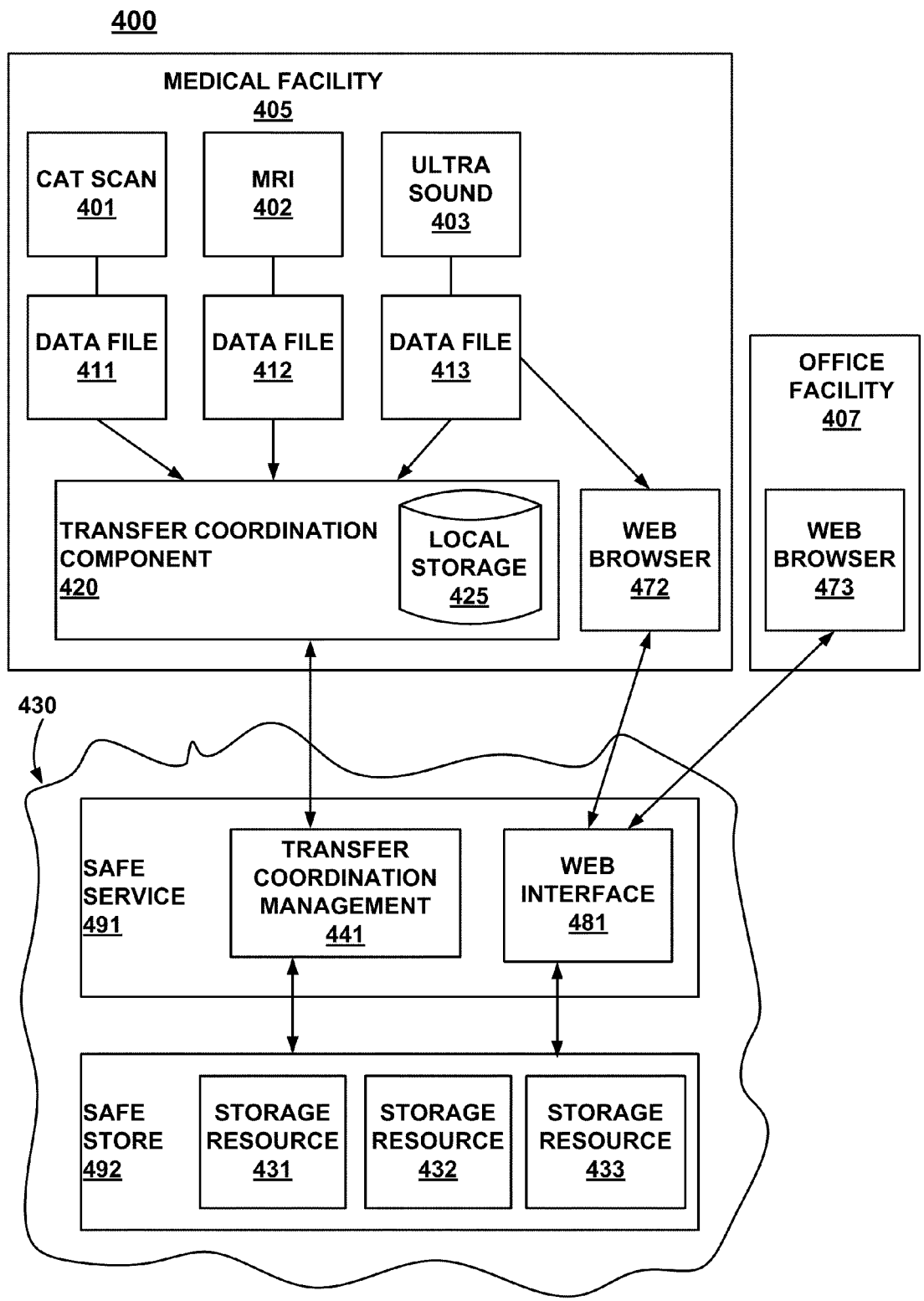
FIG. 4 is a block diagram of an exemplary data storage system in accordance with one embodiment of the present invention.

FIG. 4 is a block diagram of exemplary data storage system 400 in accordance with one embodiment of the present invention. In one embodiment, data storage system 400 is similar to data storage system 100. Data storage system 400 includes data files 411, 412, and 413, transfer coordination component 420, cloud system 430, web browsers 472 and 473. Cloud system 430 includes safe service component 491 and safe store component 492. Safe service component 491 includes transfer coordination management component 441 and WEB interface 451. Safe store component 492 includes storage resource 431, 432 and 433. In one embodiment, data files 411, 412, and 413 are communicatively coupled to WEB browser 472 and transfer coordination component 420 which includes local storage 425.

It is appreciated that present systems and methods are compatible with a variety of cloud and remote resource configurations. In one embodiment, remote resources such as the WEB browsers can be included in a plurality of different remote locations. For example, data storage system 400 also includes WEB browser 473. In one embodiment, WEB browser 472 is included in a remote medical facility 405 (e.g., a hospital, a medical lab, etc.) and web browser 473 is included in a different remote office facility 407 (e.g., doctor's office, insurance company office, etc.). The components within cloud system 430 can be communicatively coupled to one another and to components outside the cloud (e.g., through transfer coordination component 420, transfer coordination management component 441, WEB interface 451, WEB browser 472, WEB browser 473, etc.). There can be a plurality of office facilities and medical facilities and data modality collection components (e.g., 401, 402, 403, etc.) can be in different facilities (e.g., hospital, lab, university, doctor's office, etc).

The components of data storage system 400 cooperatively operate to facilitate efficient and effective storage of a plurality of data files. Data files 411, 412 and 413 are generated by different modalities (e.g., CT scan component 401, MRI component 402, Ultra Sound component 403) and communicated to PACS component 415. Transfer coordination component 420 retrieves the data files from the PACS component 415.

FIG. 5 is flow chart of exemplary information storage method 500 in accordance with one embodiment of the present invention.

In block 510 a plurality of data files associated with various modalities are received. In one embodiment the storage is in a cloud environment. The data files can be received in a cloud environment from a gateway at a remote location. In one embodiment the data files are forwarded to the cloud environment from the gateway at the remote location in accordance with predetermined metrics. For example, the files can be forwarded from the gateway during low communication bandwidth conditions (e.g., when a communication link is busy with other activities, etc.). The data files can be forwarded back to the gateway when requested.

In block 520 an analysis on the data files including examining an impact of the plurality of data files on storage based upon a type of the modality. The analysis can include resource consumption analysis of the storage associated with the type of modality. For example, the analysis can include a cost analysis of the storage associated with the type of modality. It is appreciated a variety of analysis metrics and parameters can be utilized. The analysis can be based upon study activity (e.g. number of new studies by day, week month, etc.), cloud bandwidth (e.g., image bandwidth utilization by hour, day, etc.), storage utilization (e.g., by day, week month, etc.), and storage breakdown (e.g., by modality, by site, etc.).

In block 530 resulting analysis information is forwarded for presentation in convenient user interface, including an indication of the impact of the plurality of data files on the storage based upon the type of the modality. It is appreciated the resulting analysis information can be configured for a variety of presentations. Similar to the analysis, the presentations can be based upon study activity (e.g. number of new studies by day, week month, etc.), cloud bandwidth (e.g., image bandwidth utilization by hour, day, etc.), storage utilization (e.g., by day, week month, etc.), and storage breakdown (e.g., by modality, by site, etc.). In addition, resulting analysis information can be configured for a variety of presentations (e.g., as a graph, a pie chart, a table, etc.). Additional examples of presentations are set forth in following descriptions.

It is appreciated the safe store facilities can be accessed in a variety of techniques. For example the safe store facilities can be access via a dedicated access (e.g., a PACS DICOM access, etc.), a simple storage access (e.g., CIFS, NFS, etc.), a web enabled front end, etc. In one embodiment, an onsite appliance (e.g., a gateway, a transfer coordination component, etc.) can be used to interact with safe store data centers in a cloud for both the dedicated access (e.g., a PACS DICOM access, etc.) and a simple storage access.

In one embodiment, the dedicated access is directed to DICOM data files. In one embodiment, the dedicated access is the primary form of access to the appliance. With this access the appliance operates as a DICOM archive, receiving studies from PACS using the DICOM protocol. The appliance manages the DICOM conversation to receive the DICOM studies, storage within the onsite cache, and storage to the cloud. The use of DICOM for this communication can enable the PACS to use features such as routing rules and job queues that may be available for communication with other PACS and/or archives.

In order to facilitate participation in a DICOM environment, which systems are capable of communicating with it are defined by the appliance. There may be multiple PACS for modality (e.g., Radiology, Cardiology, etc.) and it's also possible that there are multiple PACS associated with each modality department. Each PACS may also have multiple servers that are capable of sending studies to the appliance. Modalities can send DICOM studies directly to the appliance. In one exemplary implementation with a variety of potential sources for DICOM studies, the appliance is able to define what systems are allowed to communicate with it. There can also be an assumption that if a system is not defined to communicate with the appliance, then the appliance is not allowed to communicate with it.

In one embodiment, the appliance can also define which DICOM services are allowed. Some services that are available include: C-Store—to store DICOM files to the appliance; C-Move—to move DICOM files or studies to/from the appliance; and Storage Commitment—transfer ownership for the study. It is appreciated that the examples not an exhaustive list. There may be some services that are not appropriate for the appliance, such as a DICOM Modality Work List query, or a DICOM Modality Performed Procedure Step message. Services not defined for the appliance, if requested, can be rejected.

In one exemplary implementation, the expected workflow is that a server within the PACS is defined to send studies to the appliance. The appliance can define this server as one that is allowed to store studies to the appliance. It is appreciated that the PACS server can also define the appliance in order to send studies to it, so the appliance can have a way to make its DICOM connection information, usually the AE Title and TCP/IP address, available to the PACS Administrator.

In one embodiment, once the systems are defined to communicate with one another, a DICOM conversation or transaction can begin. In one exemplary implementation, the DICOM conversation can include the following operations. The PACS server initiates a DICOM negotiation association with the appliance to notify the intent to use the C-Store service to store images from a study to the appliance. If the PACS server is defined for the DICOM C-Store service the appliance accepts the association, otherwise the association is rejected. Upon acceptance, the PACS server will begin sending images to the appliance via the DICOM C-Store service.

When transmission is complete, the PACS server will close the association with the appliance. Optionally, the PACS server may also negotiate the Storage Commitment service. If accepted, the appliance accepts ownership of the study. The PACS server is then allowed to delete the study. The PACS server may negotiate the Storage Commitment service in the same association as the C-Store, or it may use a separate negotiation.

In one embodiment, DICOM is also used to retrieve studies from the cloud. The PACS can perform a DICOM Query/Retrieve to the appliance, which will then either retrieve the studies from its onsite cache or from the cloud and return them to the PACS.

DICOM Query/Retrieve (e.g., C-Find, etc.) is another service that can be defined for each server that communicates with the appliance. It is appreciated that an implementation can be configured for less than all servers to be able to query/retrieve from the appliance. For example, in certain circumstances a modality might be defined to send studies directly to the appliance, but it is unlikely that the modality will (or should) negotiate the ability to query/retrieve from the appliance.

The appliance can implement a rules-based engine to determine what studies need to be kept in the onsite cache and for how long, as well as what studies are to be migrated to the cloud and when. The appliance can keep track of where the studies are kept as the PACS can query the appliance when a study is needed from the long term archive. The appliance can be responsible for retrieving the study from the cloud if it does not exist in the onsite cache, and returning it to the PACS.

In addition, the appliance can implement an analysis of the DICOM "conversations" to determine the retrieval patterns of the studies. The administrators can then use the retrieval patterns as input to the rules-based engine to make the best use of storage to the onsite cache.

It is appreciated that the present systems and methods can include other access techniques if a facility (e.g., hospital, PACS environments, etc.) is not able to utilize the appliance as a DICOM archive. In order to allow environments such as these to take advantage of storage as a service, the appliance can offer the ability to have the PACS store its data to the appliance as though it were writing to a disk on the network. The appliance can offer the disk space through the CIFS or NFS protocols to the PACS systems. The PACS can then write the study data to the cloud in the same manner that it would write to any disk space attached to it.

For this access, it is important that what the PACS writes to the disk they are the actual DICOM files that contain the patient and study metadata, as well as the images. This is important for the web access to work properly. As a result, the appliance can check the incoming files to ensure that they are in fact DICOM files before transmitting them to the cloud.

In one embodiment, to retrieve the data from the cloud, the PACS simply reads from the appliance as though it was reading from disk. The appliance can again implement a rules-based engine to determine the contents of the onsite cache. The retrieval patterns can be determined by analyzing the read access to files from the PACS rather than the DICOM conversations.

Writing DICOM study data to the cloud can facilitate utilization of Disaster Recovery services for users. In addition, having multiple data centers geographically distributed can allow replication of the customer data so that it is available even if a single data center is affected by a disaster. This replication can happen between data centers within the cloud, and without necessarily being implemented by the appliance. The appliance can send its data to a primary data center that it is expected to communicate with. The appliance can also have an alternate path to an alternate data center in the event that the primary data center is unavailable.

In one embodiment, once the study data has been written to the safe store in the cloud, a web-based front end can be utilized for viewing the data in the cloud. At the very least, this can be utilized by users to verify that the studies are in the cloud and can be retrieved. It can also be beneficial to referring physicians that do not have access to PACS and wish to view data from the cloud. Patient access can also be possible through web access so that patients can view their own images.

In one embodiment, DICOM defines a method for accessing images through the web known as Web Access to DICOM Objects (WADO). This standard defines the method for constructing a URL to extract DICOM objects from an archive, and provides for the studies/images to be returned using standard web protocols. As there are many webproducts that support WADO, this would allow the safe store cloud to support a variety of web product that supports the standard.

It is appreciated that a variety of different analysis can be performed and results provided in a variety of different presentations. In one embodiment, aggregate statistics about the information (e.g., medical images, etc.) are presented. Meta data included in the information is examined. For example, the application can examine DICOM meta data included in each image to populate a dimensional model in a database. From the dimensional model calculations can be performed and the results presented and a user can "drill" down through a dimension to obtain more detailed information. In one embodiment a user can navigate between summary and details in a presentation. Capacity issues associated with different metrics (e.g., "days full", etc.) can be identified. Various alerts (e.g., visual alert, audio alert, e-mail alert, etc.) can be implemented to facilitate management of bandwidth and storage resources. Various presentations (e.g., charts, graphs, etc.) can be utilized to evaluate bandwidth and storage trends. Various different types of bandwidth and storage utilization analysis can be performed (e.g., by modalility, provider, site, facility, time frame, etc.). Analysis and results can be automatically ported to other applications (e.g., spreadsheet applications, word processing applications, etc.).

Figure 6:
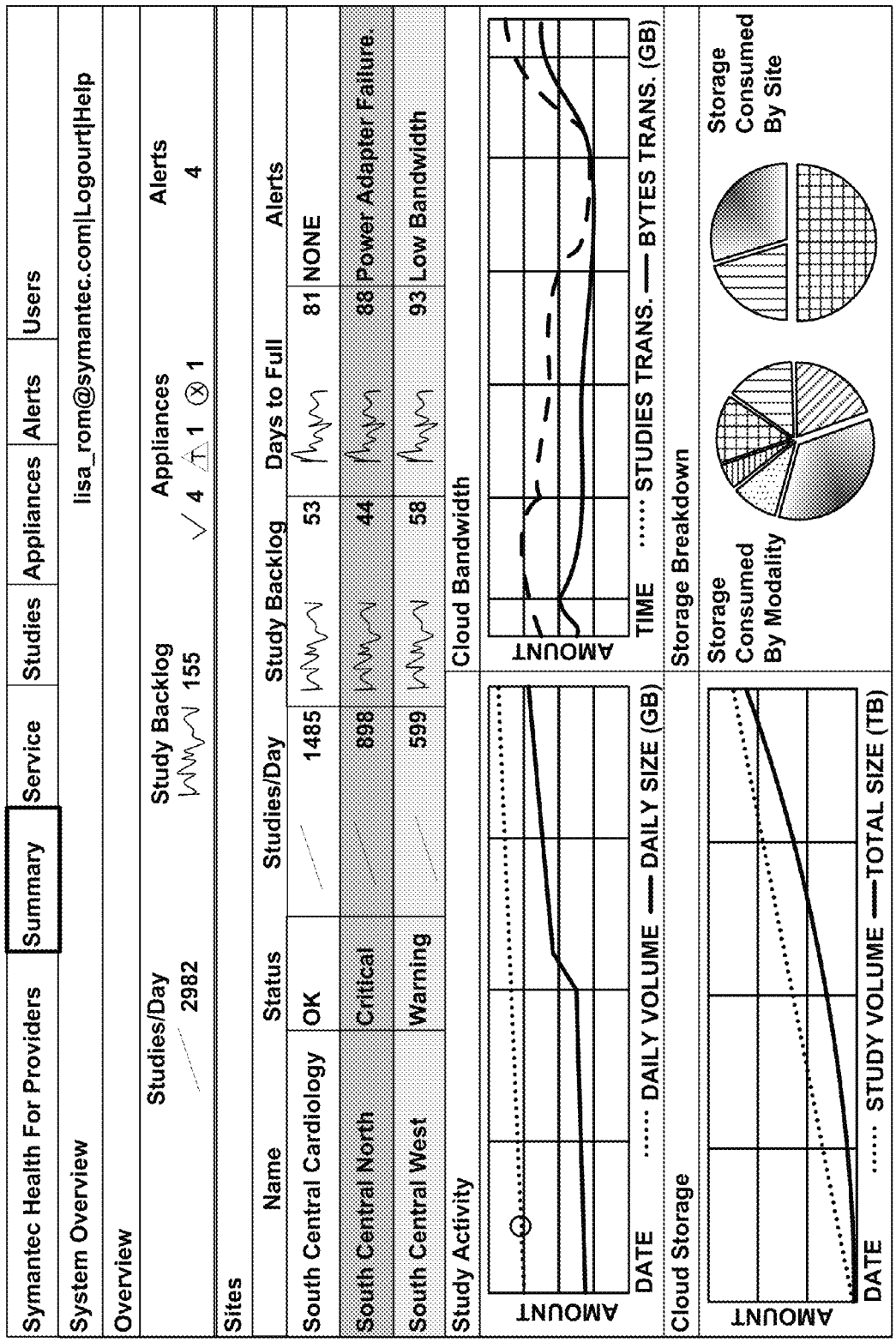
FIG. 6 is a block diagram of an exemplary summary management dashboard presentation in accordance with one embodiment of the present invention.

FIG. 6 is a block diagram of an exemplary summary management dashboard presentation in accordance with one embodiment of the present invention. The summary management dashboard presentation includes an overview section, a sites section, a study activity section, a cloud bandwidth section, a cloud storage section and a storage breakdown section. The overview section includes indications of the studies per day, the study backlog, appliances and alerts. The sites section includes the names of various sites or facilities and indications of various characteristics or metrics (e.g., status, studies per day, study backlog, days to full alerts, etc.) per site.

Figure 7:
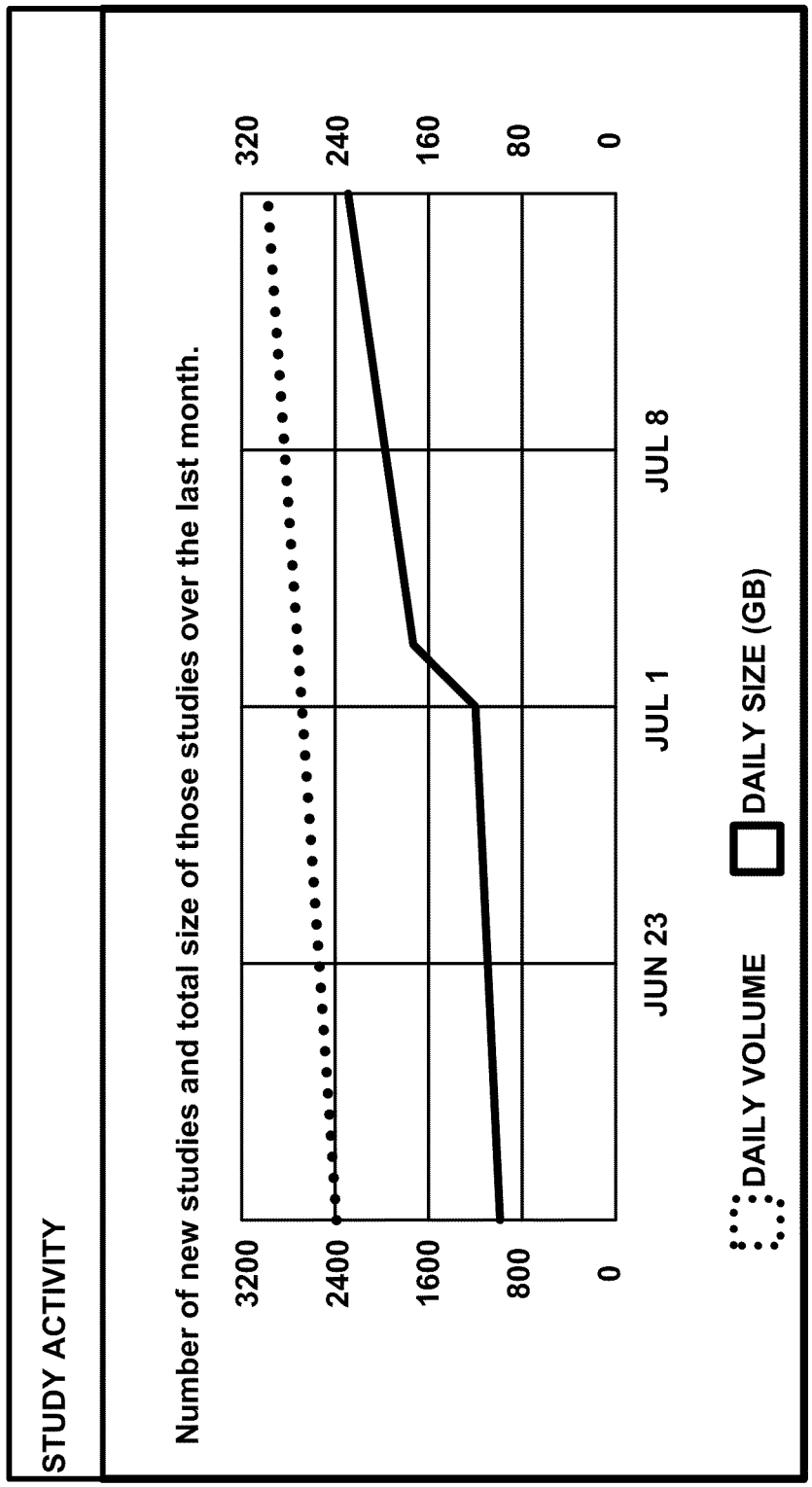
FIG. 7 is a block diagram of an exemplary study activity presentation including total volume and size of studies received by a safe store for a month in accordance with one embodiment of the present invention.

In one embodiment, a presentation includes an indication of study activity during a particular time frame. FIG. 7 is a block diagram of an exemplary study activity presentation including total volume and size of studies received by a safe store for a month. The presentation includes a graph with a y axis indicating the number of studies and the x-axis indicating the days of the month. The graph can include multiple indication lines. For example, the graph can include a line corresponding to daily volume and another line corresponding to daily size.

Figure 8:
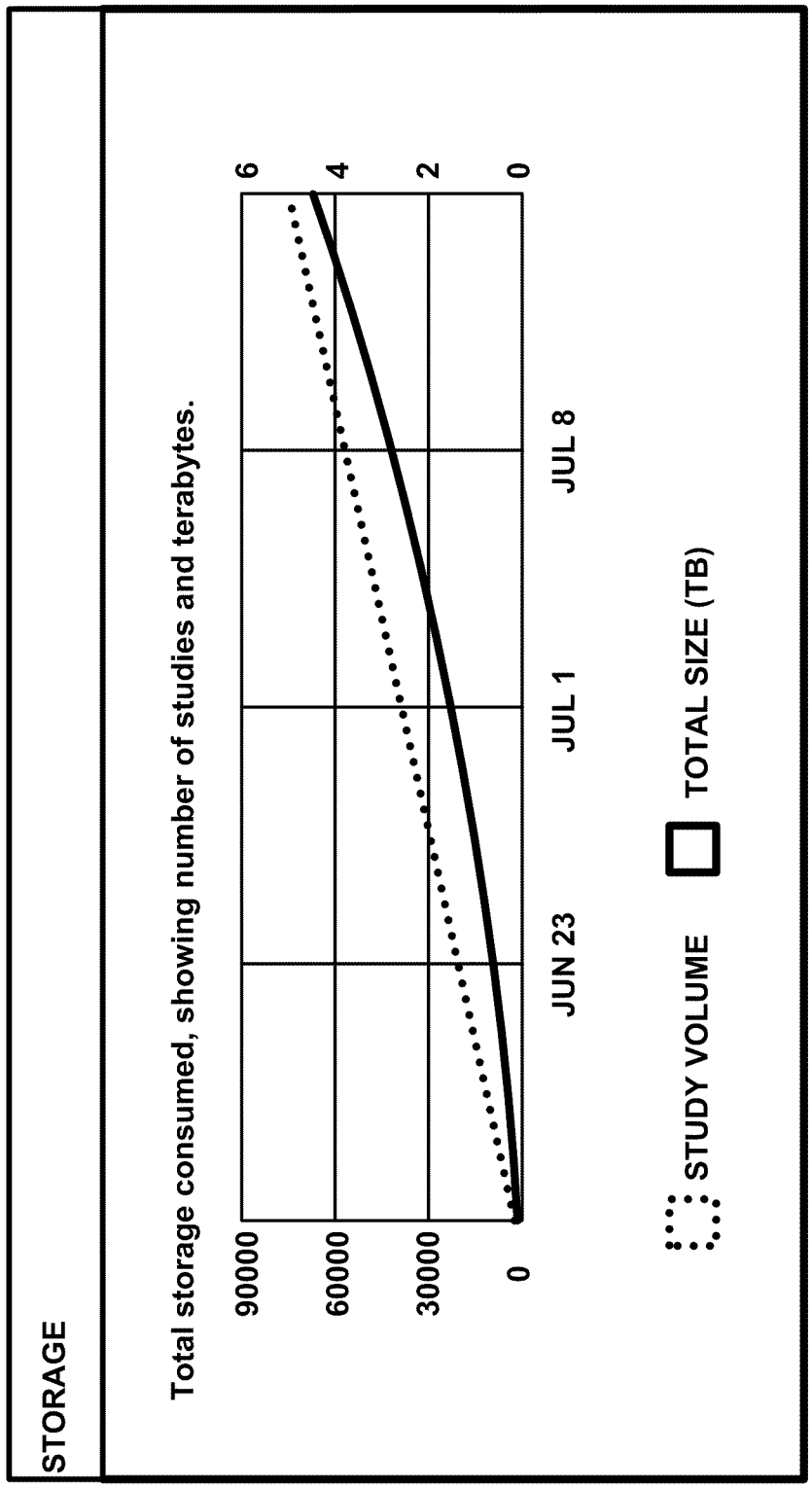
FIG. 8 is a block diagram of an exemplary storage consumption presentation including weekly storage consumed for a month in accordance with one embodiment of the present invention.

In one embodiment, a presentation includes an indication of storage consumption for a given time frame. FIG. 8 is a block diagram of an exemplary storage consumption presentation including weekly storage consumed for a month. The presentation includes a graph with a y axis indicating the amount of storage and the x-axis indicating the days of the month. Again, the graph can include multiple indication lines. For example, the graph can include a line corresponding to daily volume and another line corresponding to daily size.

Figure 9:
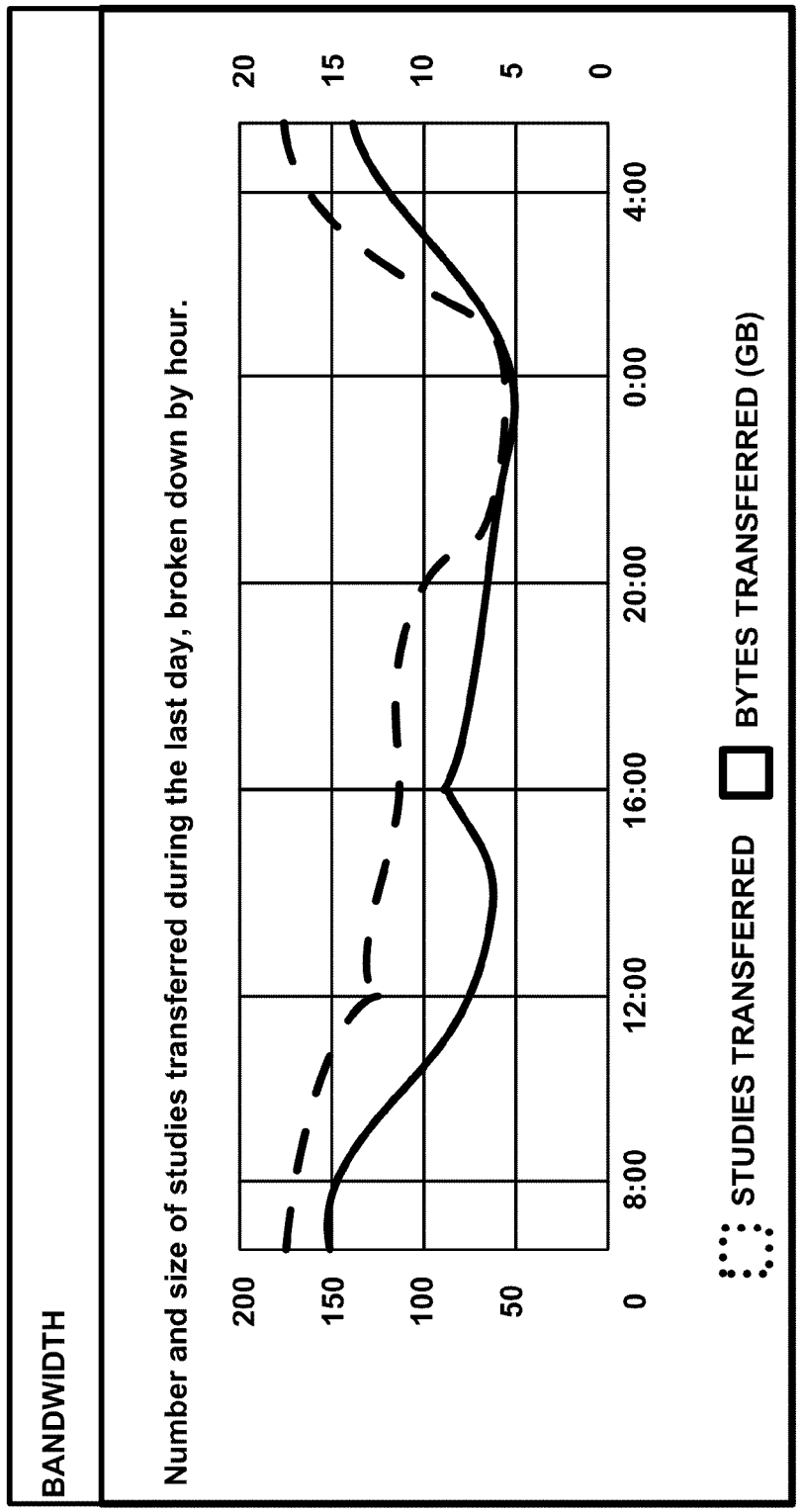
FIG. 9 is a block diagram of an exemplary bandwidth utilization presentation including image bandwidth utilization for an hour in accordance with one embodiment of the present invention.

In one embodiment, a presentation includes an indication of bandwidth utilized for a given time frame. FIG. 9 is a block diagram of an exemplary bandwidth utilization presentation including image bandwidth utilization for an hour. The presentation includes a graph with a y axis indicating the amount of bandwidth and the x-axis indicating the hour of the day. Again, the graph can include multiple indication lines. For example, the graph can include a line corresponding to daily volume and another line corresponding to daily size.

Figure 10:
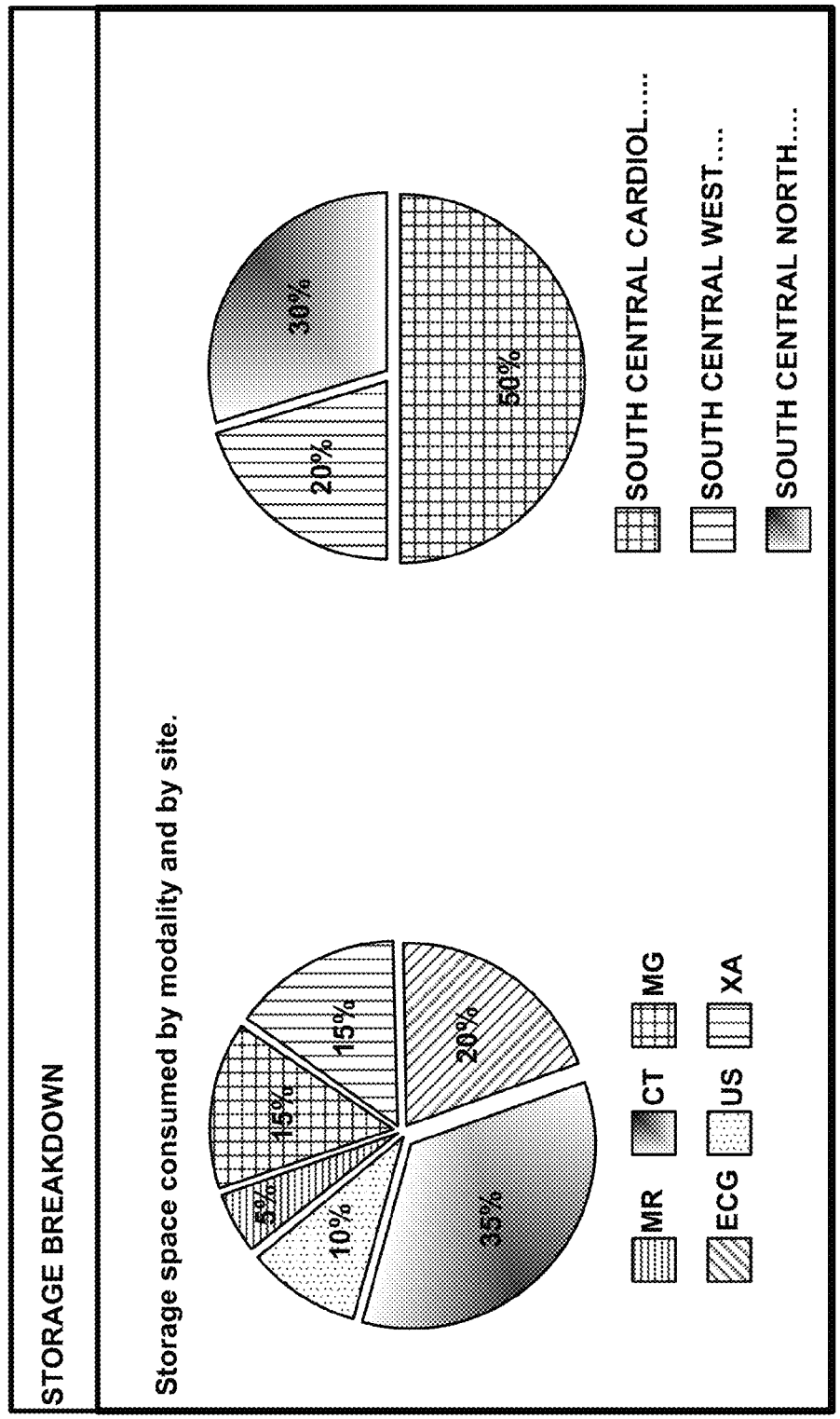
FIG. 10 is a block diagram of an exemplary storage utilization by type of modality presentation including storage utilized by modality and further indication by site or facility in accordance with one embodiment of the present invention.

In one embodiment, a presentation includes an indication of storage utilization by type of modality. FIG. 10 is a block diagram of an exemplary storage utilization by type of modality presentation including storage utilized by modality and further indication by site or facility. It is appreciated that analysis information can be presented in a variety of charts or graphs. In FIG. 10, the presentation includes a pie chart for types of modality and another for site or facility. For user convenience, keys can be provided to assist in interpreting the charts and information.

In one embodiment, a presentation includes an indication of appliance metrics by site and status selection. FIG. 11 is a block diagram of an exemplary appliance metrics by site and status selection presentation. It is appreciated that analysis information can be presented in a variety of tables also. In FIG. 11, the presentation includes a table for appliance metrics by site and status selection. The presentation can also include query controls.

Figure 12:
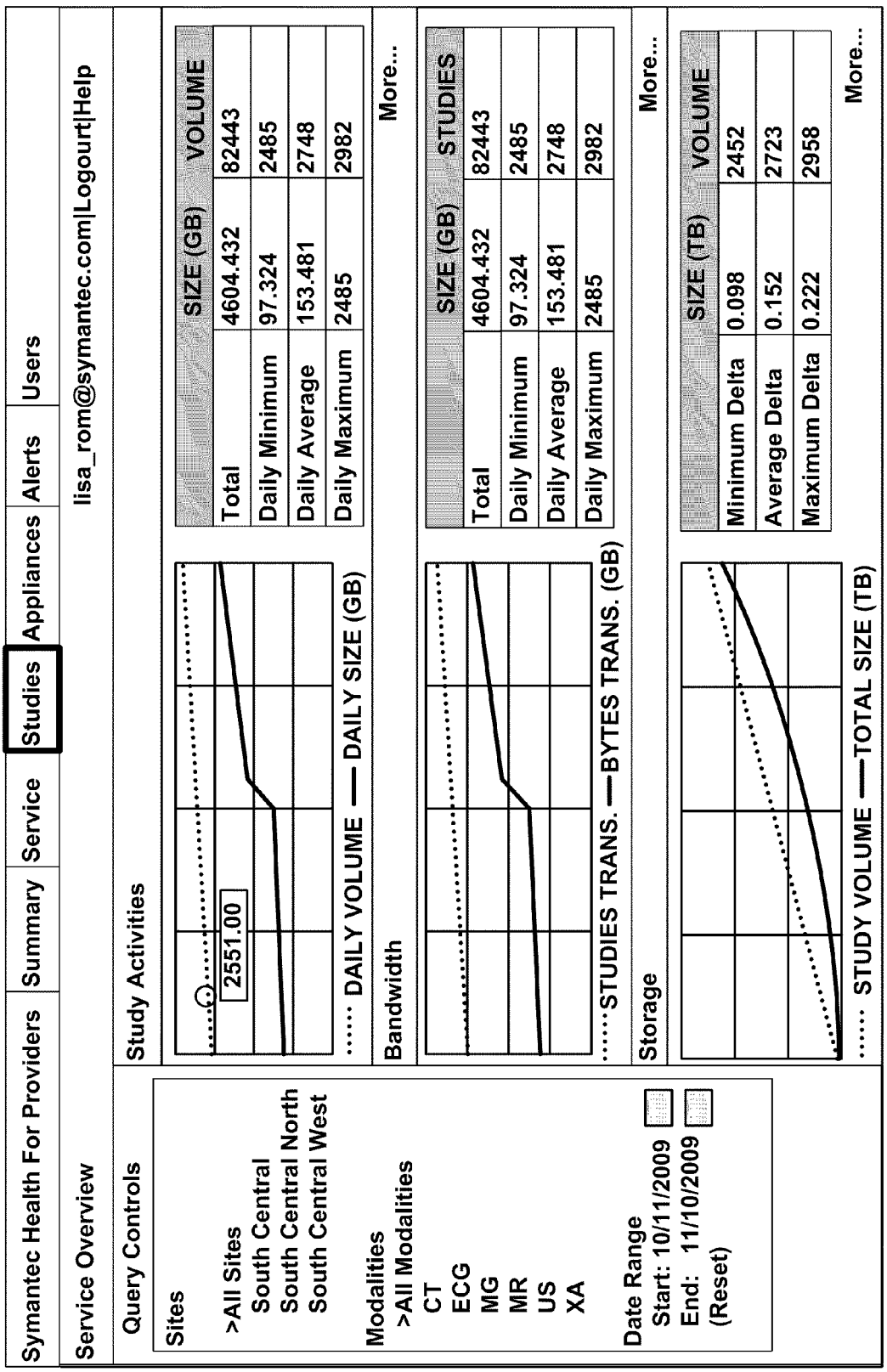
FIG. 12 is a block diagram of an exemplary presentation that includes study, bandwidth and storage metrics by site, modality and date range selection in accordance with one embodiment of the present invention.

In one embodiment, a presentation can include a combination of various different charts and information for convenient comparison. FIG. 12 is a block diagram of an exemplary presentation that includes study, bandwidth and storage metrics by site, modality and date range selection. It is appreciated that analysis information can be presented in a variety of tables, graphs, charts, etc. Again, the presentation can also include query controls.

Figure 13:
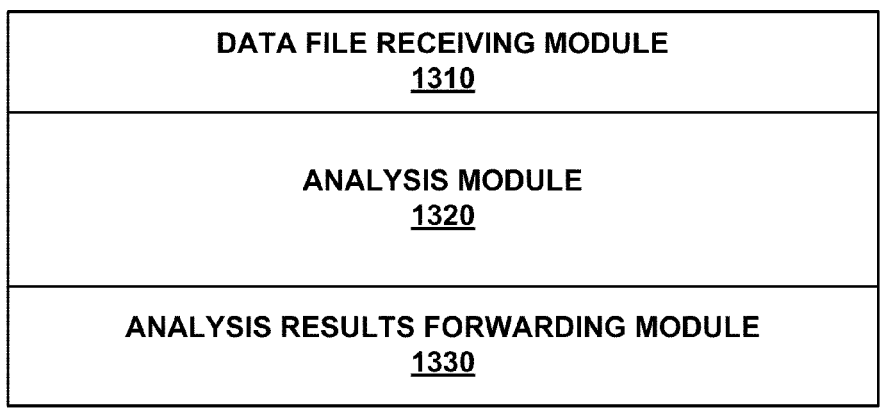
FIG. 13 is a block diagram of an exemplary storage module in accordance with one embodiment of the present invention.

FIG. 13 is a block diagram of storage module 1300 which includes instructions for directing a processor in performance of a storage method (e.g., a storage method 100, 500, etc.). Storage module 1300 includes data file receiving module 1310, analysis module 1320, and analysis results forwarding module 1330. Storage module 1310 includes instructions for receiving a plurality of data files. In one embodiment, detection module 1310 includes instructions for receiving a plurality of data files as indicated in blocks 210 and 510. Analysis module 1320 includes instructions for performing analysis on the data files including examining an impact of the plurality of data files on storage. In one embodiment, analysis module 820 includes instructions for performing analysis indicated in block 220 and 520. Analysis results forwarding module 1330 includes instructions for forwarding resulting analysis information for presentation in a convenient user interface. In one embodiment, reply module 1330 includes instructions for forwarding resulting analysis information for presentation in a convenient user interface as indicated in block 230 and 530.

Figure 14:
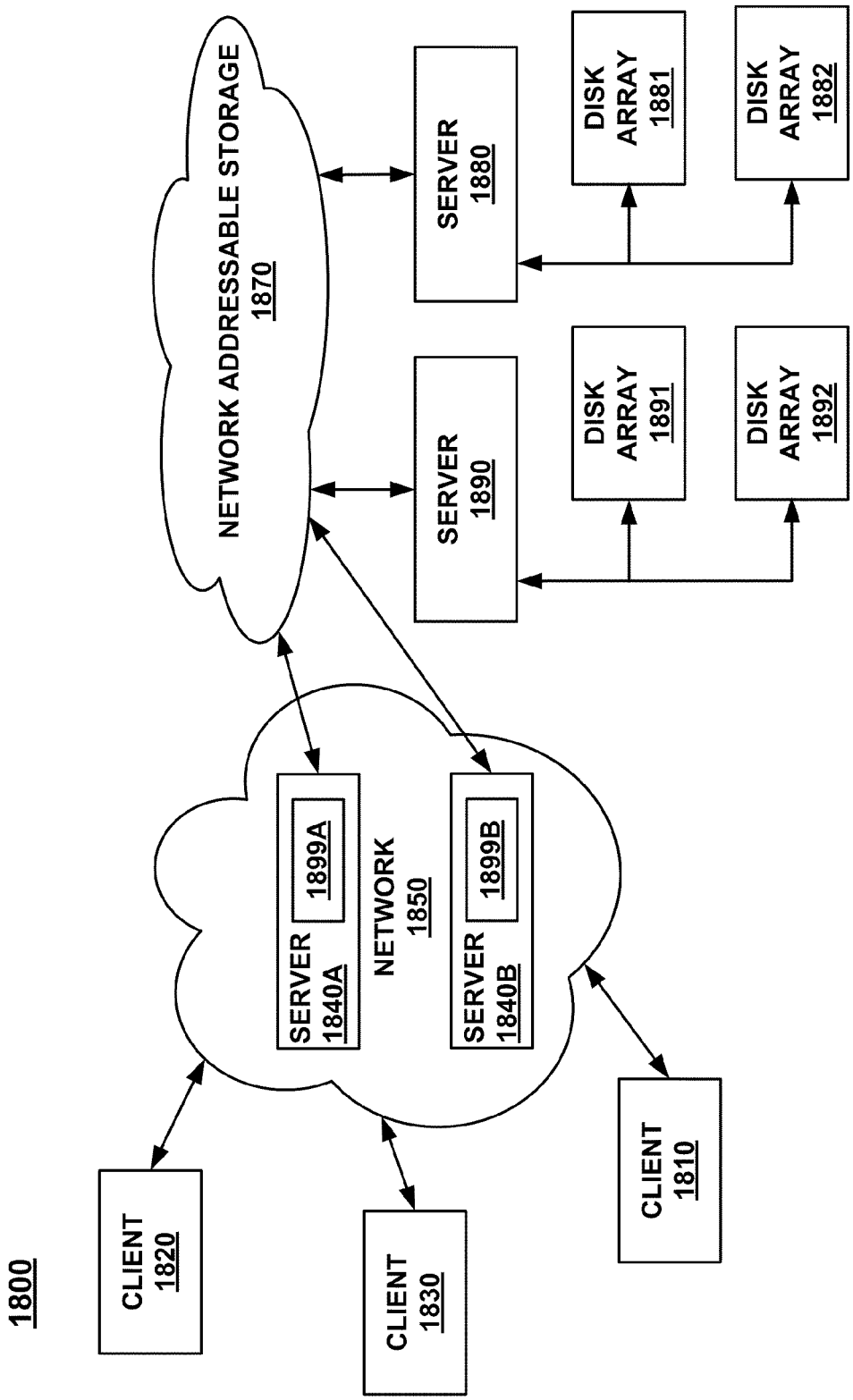
FIG. 14 is a block diagram of an exemplary network architecture in accordance with one embodiment of the present invention.

In one embodiment, a storage method (e.g., storage method 100, 500) can be implemented on a network. FIG. 14 is a block diagram depicting a network architecture 1800 in which client systems 1810, 1820 and 1830, as well as network addressable storage 170, are coupled to a network 1850. Network 1850 includes storage servers 1840A and 1840B (any of which can be implemented using computer system 210). Network addressable storage 170 includes storage servers 1890 and 1880 (any of which can be implemented using computer system 1110). Storage server 1890 is further depicted as having storage devices 1891 and 1892 directly attached, and storage server 1880 is depicted with storage devices 1881 and 1882 directly attached. Client systems 1810, 1820 and 1830 can access network addressable storage 1870 via servers 1840A and 1840B of network 1850. In one embodiment, server 1840A and 1840B include storage modules 1899A and 1899B respectively. In one embodiment, storage modules 1899A and 1899B are similar to similar to storage module 1300. It is appreciated that present systems and methods are compatible with a variety of implementations. For example, portions of information and instructions associated with can be distributed in various resources.

Figure 15:
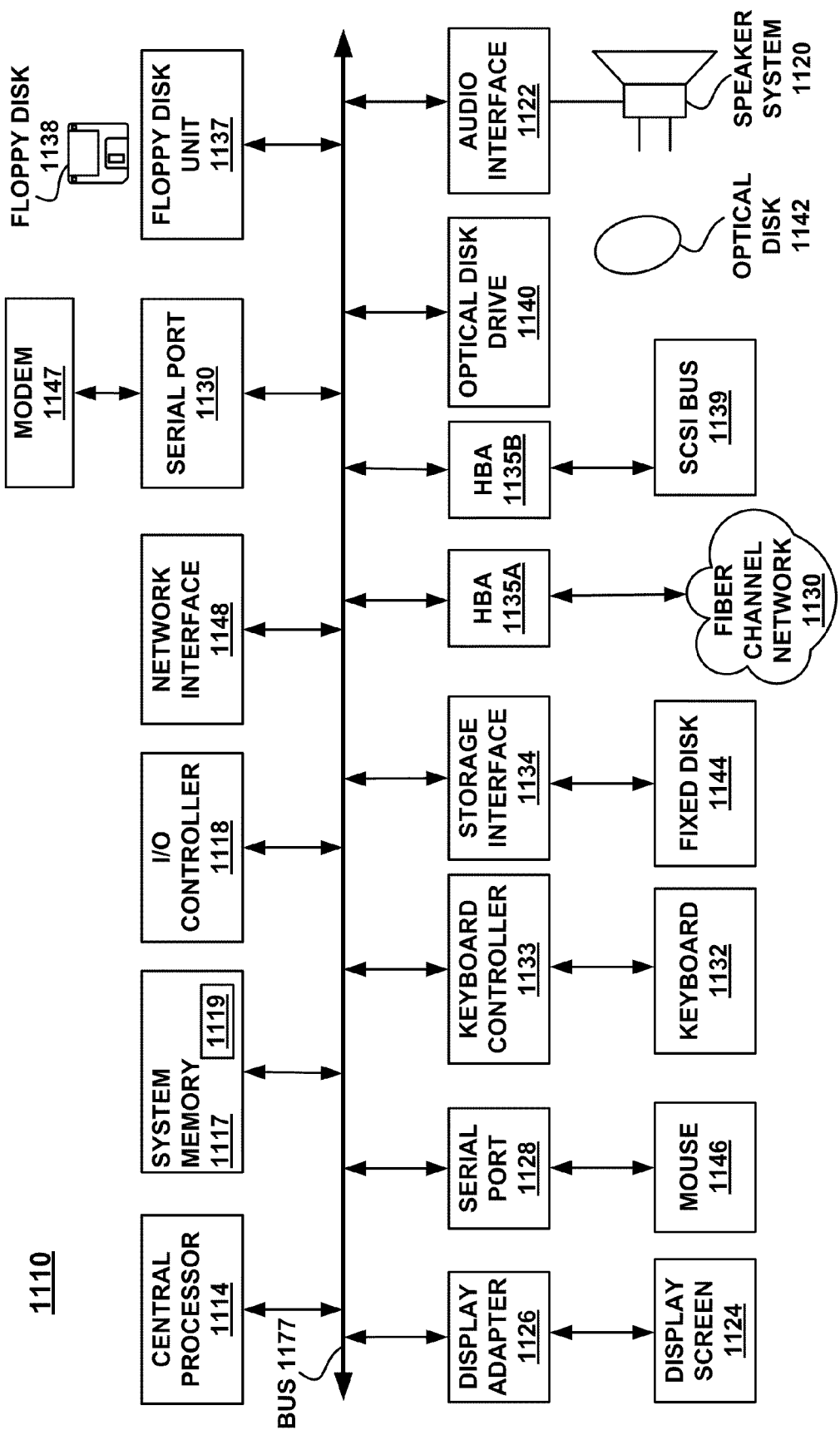
FIG. 15 depicts a block diagram of an exemplary computer system suitable for implementing the present methods in accordance with one embodiment of the present invention.

FIG. 15 depicts a block diagram of an exemplary computer system 1110 suitable for implementing the present methods. Computer system 1110 includes a bus 1177 which interconnects major subsystems of computer system 1110, such as a central processor 1114, a system memory 1117 (typically RAM, but which may also include ROM, flash RAM, or the like), an input/output controller 1118, an external audio device, such as a speaker system 1120 via an audio output interface 1122, an external device, such as a display screen 1124 via display adapter 1126, serial ports 1128 and 1130, a keyboard 1132 (interfaced with a keyboard controller 1133), a storage interface 1134, a floppy disk drive 1137 operative to receive a floppy disk 1138, a host bus adapter (HBA) interface card 1135A operative to connect with a Fiber Channel network 1190, a host bus adapter (HBA) interface card 1135B operative to connect to a SCSI bus 1139, and an optical disk drive 1140 operative to receive an optical disk 1142. Also included are a mouse 1146 or other point-and-click device (coupled to bus 1112 via serial port 1128), a modem 1147 (coupled to bus 1112 via serial port 1130), and a network interface 1148 (coupled directly to bus 1112).

Bus 1177 allows data communication between central processor 1114 and system memory 1117, which may include read-only memory (ROM) or flash memory (neither shown), and random access memory (RAM) (not shown), as previously noted. In one embodiment, instructions for performing a storage method (e.g., similar to storage method 200 etc.) are stored in one or more memories of computer system 1100 (e.g., in memory location 1119). The RAM is generally the main memory into which the operating system and application programs are loaded. In one embodiment, RAM 1117 includes a reference count update module (e.g., in memory location 1119). In one embodiment, a reference storage module stored in memory location 1119 is similar to storage module 1300. The ROM or flash memory can contain, among other code, the Basic Input-Output system (BIOS) which controls basic hardware operation such as the interaction with peripheral components. Applications resident with computer system 1110 are generally stored on and accessed via a computer readable medium, such as a hard disk drive (e.g., fixed disk 1144), an optical drive (e.g., optical drive 1140), floppy disk unit 1137, or other storage medium. Additionally, applications can be in the form of electronic signals modulated in accordance with the application and data communication technology when accessed via network modem 1147 or interface 248.

Storage interface 1134, as with the other storage interfaces of computer system 1110, can connect to a standard computer readable medium for storage and/or retrieval of information, such as a fixed disk drive 1144. Fixed disk drive 1144 may be a part of computer system 1110 or may be separate and accessed through other interface systems. Modem 1147 may provide a direct connection to a remote server via a telephone link or to the Internet via an internet service provider (ISP). Network interface 1148 may provide a direct connection to a remote server via a direct network link to the Internet via a POP (point of presence). Network interface 1148 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). Conversely, all of the devices shown in FIG. 15 need not be present to practice the present disclosure. The devices and subsystems can be interconnected in different ways from that shown in FIG. 15. Code to implement the present disclosure can be stored in computer-readable storage media such as one or more of system memory 1117, fixed disk 1144, optical disk 1142, or floppy disk 1138. In one embodiment, computer-readable storage media includes re-programmable non-transitory storage media. The operating system provided on computer system 1110 may be MS-DOS®, MS-WINDOWS®, OS/2®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present disclosure may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

With reference to computer system 1110, modem 1147, network interface 1148 or some other method can be used to provide connectivity from each of client computer systems 1810, 1820 and 1830 to network 1850. Client systems 1810, 1820 and 1830 are able to access information on network addressable storage using, for example, a transfer coordination component, a web browser, or other client software (not shown). Such a client allows client systems 1810, 1820 and 1830 to access data hosted by storage server 1840 or 1880 or one of the corresponding storage devices. FIG. 14 depicts the use of a network such as the Internet for exchanging data, but the present disclosure is not limited to the Internet or any particular network-based environment.

Thus, the present systems and methods facilitate efficient and effective data storage and impact analysis on storage facilities. Present systems and methods facilitate cost assignment and cost analysis associated with storage of the data. Present system and method archiving solutions can compliment existing infrastructures. The secure alternative to onsite storage can provide pay per usage capacity on demand to facilitate reduction of costs and capital spending. Multiple images or copies can be archived in a plurality of resources (e.g., geographically distributed, high availability, etc.) utilized for data recovery.

Portions of the detailed description are presented and discussed in terms of a method. Although steps and sequencing thereof are disclosed in figures herein describing the operations of this method, such steps and sequencing are exemplary. Embodiments are well suited to performing various other steps or variations of the steps recited in the flowchart of the figure herein, and in a sequence other than that depicted and described herein. Some portions of the detailed description are presented in terms of procedures, steps, logic blocks, processing, and other symbolic representations of operations on data bits that can be performed within a computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps include physical manipulations of physical quantities. Usually, though not necessarily, these quantities take the form of electrical, magnetic, optical or quantum signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "processing", "computing", "calculating", "determining", "displaying", "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Computing devices can include at least some form of computer readable media. Computer readable media can be any available media that can be accessed by a computing device. By way of example, and not limitation, computer readable medium may comprise computer storage media. Computer storage media includes volatile and nonvolatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile discs (DVD) or other optical storage, magnetic cassettes, magnetic tape, magnetic disk storage or other magnetic storage devices, or any other medium which can be used to store the desired information and which can be accessed by a computing device. Communication media typically embodies carrier waves or other transport mechanism and includes any information delivery media. By way of example, and not limitation, communication media includes wired media such as a wired network or direct-wired connection, and wireless media such as acoustic, RF, infrared, other wireless media, and combinations of any of the above.

Some embodiments may be described in the general context of computer-executable instructions, such as program modules, executed by one or more computers or other devices. Generally, program modules include routines, programs, objects, components, data structures, etc, that perform particular tasks or implement particular abstract data types. The functionality of the program modules may be combined or distributed as desired in various embodiments.

The foregoing descriptions of specific embodiments have been presented for purposes of illustration and description. They are not intended to be exhaustive or to limit the invention to the precise forms disclosed, and many modifications and variations are possible in light of the above teaching. The embodiments were chosen and described in order to best explain the principles and its practical application, to thereby enable others skilled in the art to best utilize the invention and various embodiments with various modifications as are suited to the particular use contemplated. It is intended that the scope be defined by the Claims appended hereto and their equivalents.

What is claimed is:

1. An information storage method comprising:
   receiving a plurality of data files associated with various medical modalities and various medical studies, wherein the plurality of data files are further associated with various sites, wherein the plurality of data files are received in a cloud environment from a gateway at a remote location, wherein said plurality of data files are forwarded to said cloud environment from said gateway at said remote location in accordance with a predetermined metric, wherein the predetermined metric is an amount of storage resources occupied;
   performing an a modality type impact analysis on said plurality of data files including examining an impact of said plurality of data files on storage based upon a type of said medical modality;
   performing a site impact analysis on said plurality of data files including examining an impact of said plurality of data files on storage based upon one or more sites associated with each of said plurality of data files; and
   forwarding resulting analysis information for presentation in a user interface, including an indication of said impact of said plurality of data files on said storage based upon said type of said medical modality and an indication of said impact of said plurality of data files on said storage based upon one or more sites associated with each of said plurality of data files.

2. The information storage method of claim 1 wherein said storage is in a cloud environment.

3. The information storage method of claim 1 wherein said analysis includes resource consumption analysis of said storage associated with said type of medical modality.

4. The information storage method of claim 1 wherein said analysis includes a cost analysis of said storage associated with said type of medical modality.

5. The information storage method of claim 1 further comprising forwarding said data files back to said gateway when requested.

6. A non-transitory computer readable storage medium having stored thereon computer executable instructions that, when executed by a computer system cause the computer system to perform a method comprising:
   receiving a plurality of data files associated with various medical modalities and various medical studies, wherein the plurality of data files are further associated with various sites, wherein the plurality of data files are received in a cloud environment from a gateway at a remote location, wherein said plurality of data files are forwarded to said cloud environment from said gateway at said remote location in accordance with a predetermined metric, wherein the predetermined metric is an amount of storage resources occupied;
   performing an analysis on said plurality of data files including examining an impact of said plurality of data files on storage based upon a type of said medical modality;
   performing a site impact analysis on said plurality of data files including examining an impact of said plurality of data files on storage based upon one or more sites associated with each of said plurality of data files; and
   forwarding resulting analysis information for presentation in a user interface, including an indication of said impact of said plurality of data files on said storage based upon said type of said medical modality and an indication of said impact of said plurality of data files on said storage based upon one or more sites associated with each of said plurality of data files.

7. The non-transitory computer associated readable storage medium of claim 6 wherein said analysis includes resource consumption analysis of said storage associated with said type of medical modality.

8. The non-transitory computer readable storage medium of claim 6 wherein said analysis includes a cost analysis of said storage associated with said type of medical modality.

9. The non-transitory computer readable storage medium of claim 8 wherein said data files are forwarded back to said gateway when requested.

10. A computer system, comprising:
    a computer system having a processor coupled to a computer readable storage media and executing computer readable code which causes the computer system to perform operations including:
      receiving a plurality of data files associated with various medical modalities and various medical studies, wherein the plurality of data files are further associated with various sites, wherein the plurality of data files are received in a cloud environment from a gateway at a remote location, wherein said plurality of data files are forwarded to said cloud environment from said gateway at said remote location in accordance with a predetermined metric, wherein the predetermined metric is an amount of storage resources occupied;
      performing an analysis on said plurality of data files including examining an impact of said plurality of data files on storage based upon a type of said medical modality;
      performing a site impact analysis on said plurality of data files including examining an impact of said plurality of data files on storage based upon one or more sites associated with each of said plurality of data files; and
      forwarding resulting analysis information for presentation in a user interface, including an indication of said impact of said plurality of data files on said storage based upon said type of said medical modality and an indication of said impact of said plurality of data files on said storage based upon one or more sites associated with each of said plurality of data files.

11. The computer system of claim 10 wherein said analysis includes resource consumption analysis of said storage associated with said type of medical modality.

12. The computer system of claim 10 wherein said analysis includes a cost analysis of said storage associated with said type of medical modality.

13. The computer system of claim 10 further wherein said data files are forwarded back to said gateway when requested.

\* \* \* \* \*